United States Patent [19]

Nosé et al.

[11] Patent Number: 5,713,730
[45] Date of Patent: Feb. 3, 1998

[54] CERAMIC PIVOT BEARING ARRANGEMENT FOR A SEALLESS BLOOD PUMP

[75] Inventors: Yukihiko Nosé; Setsuo Takatani, both of Houston, Tex.; Ichiro Sakuma, Tsurugashima, Japan; Yasuhisa Ohara; Kenzo Makinouchi, both of Houston, Tex.

[73] Assignees: Kyocera Corporation, Kyoto, Japan; Baylor College of Medicine, Houston, Tex.

[21] Appl. No.: 437,553

[22] Filed: May 2, 1995

Related U.S. Application Data

[63] Continuation-in-part of Ser. No. 401,567, Mar. 9, 1995, abandoned, which is a continuation-in-part of Ser. No. 940,510, Apr. 4, 1992, Pat. No. 5,399,074.

[51] Int. Cl.$^6$ .................................................. F04B 35/04
[52] U.S. Cl. ........................... 417/423.12; 417/424.2; 417/423.15; 417/423.14
[58] Field of Search ........................ 417/423.1, 423.7, 417/423.15, 423.12, 423.14, 424.1, 424.2

[56] References Cited

U.S. PATENT DOCUMENTS

| 4,507,048 | 3/1985 | Belenger et al. ................. 415/90 |
| 4,688,998 | 8/1987 | Olsen et al. . |
| 4,984,972 | 1/1991 | Clansen et al. . |
| 4,994,078 | 2/1991 | Jarvik ................................. 623/3 |
| 5,092,879 | 3/1992 | Jarvik ................................. 623/3 |
| 5,601,418 | 2/1997 | Ohara et al. ................... 417/424.2 |

*Primary Examiner*—Charles G. Freay
*Attorney, Agent, or Firm*—Loeb & Loeb LLP

[57] ABSTRACT

A centrifugal blood pump, used for heart-lung machines or the like, having at least one impeller, a casing having an inlet and an outlet, the casing formed to have a space for rotatably housing the at least one impeller and a magnetic drive disposed outside the casing. The impeller may have vanes attached thereto for forcing fluid through the casing. Further the vanes may have magnets imbedded therein. The magnetic drive and the imbedded magnets cooperate to rotate the impeller. The impeller may have pivots integrated at opposing ends for allowing the impeller to rotate about a horizontal axis. The pivots may be supported by pivot bearings disposed within the casing. The pivots and the pivot bearings may be made of a ceramic material.

9 Claims, 15 Drawing Sheets

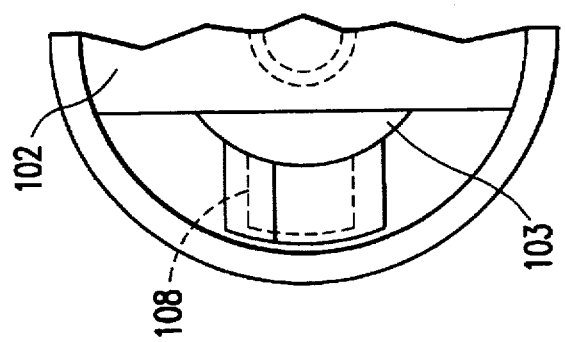
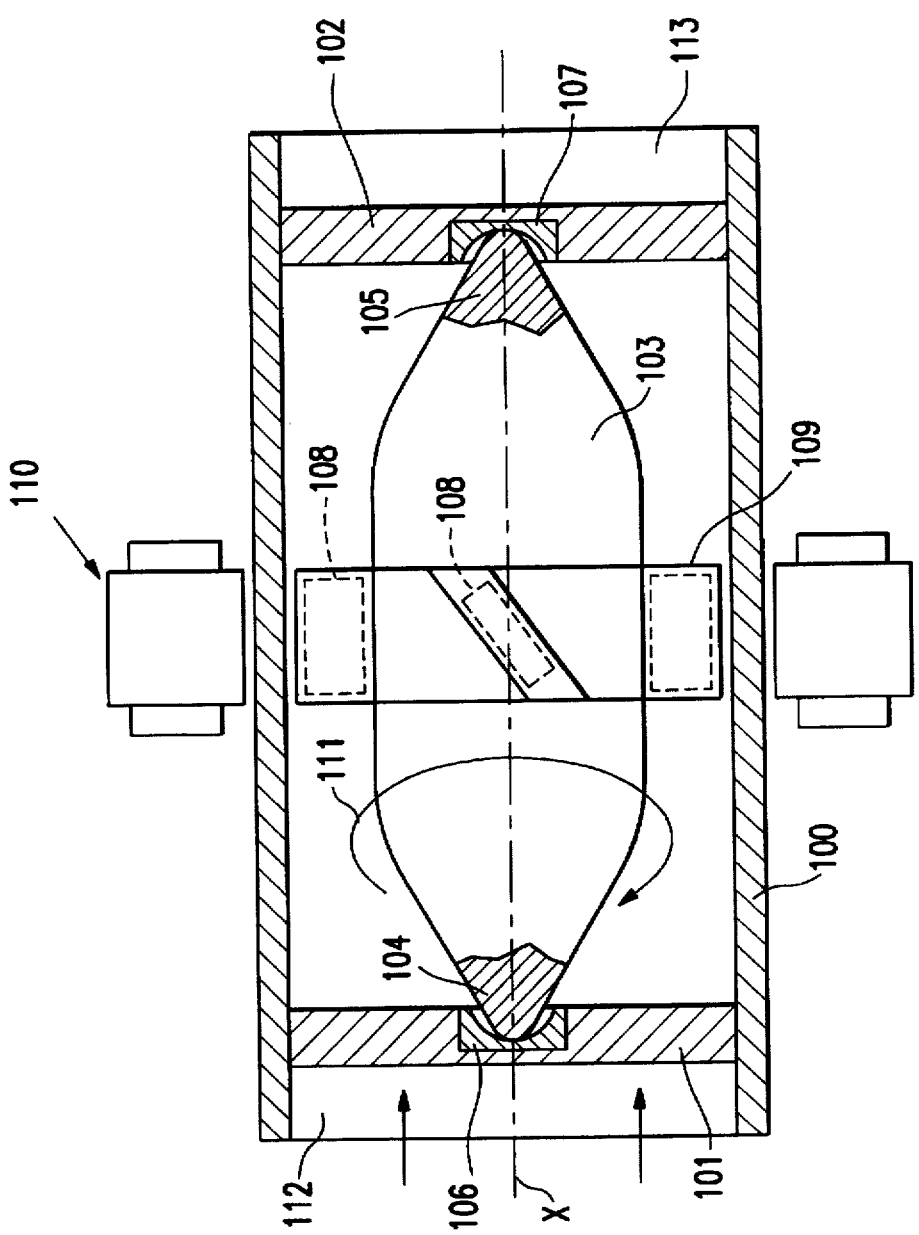
FIG. 11
FIG. 10

CERAMIC PIVOT BEARING ARRANGEMENT FOR A SEALLESS BLOOD PUMP

CROSS-REFERENCE TO RELATED APPLICATIONS

This is a continuation application of Ser. No. 08/401,567, filed Mar. 9, 1995, now abandoned, which in turn is a continuation-in-part application of Ser. No. 07/940,510, filed Sep. 4, 1992, now issued as U.S. Pat. No. 5,399,074, issued Mar. 12, 1995.

BACKGROUND OF THE INVENTION

1. Field of the Invention

The present invention relates to a centrifugal blood pump used for heart-lung machines or the like. Further, the invention related to any rotary pump such as axial flow pumps, screw pumps and mixed flow pumps, which may be used as blood pumps.

2. Related Art

Conventionally, pulsatile pumps and roller pumps were used as blood circulation pumps for heart-lung machines or the like. In recent years, centrifugal pumps which are compact, efficient and reliable have become to be used widely.

However, centrifugal blood pumps are apt to cause the problem of generating thrombi at bearings and sealing parts because of blood stagnation around the sealing parts for sealing the rotation axis of the impeller with vanes and heat generation in the sealing parts. In addition, there is the danger of leaking blood through the sealing parts. Because of these problems, the pumps cannot be operated continuously for an extended period of time.

To solve these problems, various centrifugal blood pumps have been proposed, which require no seals for the rotation shaft.

In the case of the blood pump described in the specification of U.S. Pat. No. 4,688,988, the impeller with vanes accommodated in the casing of the pump is equipped with magnets which form a part of a magnetic suspension means and magnets which form a part of a magnetic rotation means. Outside the casing, the pump is equipped with an electric magnet means disposed corresponding to the magnets of the impeller. By operating these electric magnet means, the impeller in the casing is suspended in the normal position and rotated properly. With this type of pump, however, it is difficult to control the position and suspension conditions of the impeller with vanes, causing unstable impeller rotation. Furthermore, the pump becomes complicated and large, confronting difficulty when it is put to practical use.

In the case of the blood pump described in the specification of U.S. Pat. No. 4,984,972, the boss located in the center of the impeller is mounted on the bearing supported in the pump chamber inside the housing of the disposable pumping unit of the pump, for example, the bearing formed at the top section of the conical stator of the pump, to support the impeller, and the magnets disposed around the impeller are combined magnetically to rotate the impeller and the magnetic drive means disposed outside the pumping unit. Since the impeller of this pump is supported only at a single point and the magnets are carried on the impeller, it is difficult to balance the impeller, causing unstable rotation.

In the case of the centrifugal blood pump described in the specification of U.S. Pat. No. 4,507,048, the nearly conical impeller with vanes of the pump, rotatably accommodated in the casing, is supported by the watch-type jewelled pivots formed at the upper and lower ends of the center axis thereof. On the bottom surface side of the conical impeller, a magnetic means is disposed and cooperates with the magnetic drive means disposed outside the casing to rotate the impeller. Since the center axis of the impeller of this pump is supported by the two upper and lower jewelled pivots, the impeller's dynamic balance of the pump is better than that of the pump described in the above-mentioned U.S. Pat. No. 4,984,972, ensuring stable rotation of the impeller. However, since this pump has magnets on the bottom surface of the conical impeller, it is necessary to reduce the gap between the bottom surface of the impeller and the casing to enhance the efficiency of impeller rotation obtained by the cooperation of the magnets and the magnet drive means outside the casing. As a result of reducing the gap, it is difficult for blood to flow through the gap, thereby being apt to cause a problem of generation of thrombi, particularly at the jewelled pivot on the bottom surface side of the impeller. Further, since the jewelled pivots are each made of a single crystal produced naturally, they are expensive and have low processability. In comparison, the ceramics used in the present invention are polycrystal, produced artificially and can be formed to any desired shape. The use of ceramics allows for easy production of pivots and pivot bearings. Additionally, by using ceramics, hemolytic and anti-thrombogenic characteristics can be improved significantly.

As described above, the centrifugal blood pumps having been proposed so far without using shut-off seals had various problems and could not be put to practical use.

SUMMARY OF THE INVENTION

The present invention is intended to solve the above-mentioned problems encountered in centrifugal blood pumps. An object of the present invention is to provide a centrifugal blood pump having no seals on its rotation axis and capable of stably rotating an impeller with vanes, thereby scarcely generating thrombi.

Another object of the present invention is to provide a centrifugal blood pump which scarcely causes hemolysis.

A further object of the present invention is to provide a centrifugal blood pump which scarcely generates thrombi or hemolysis and is capable of being operated for an extended period of time.

To achieve the above-mentioned objects, the blood pump provided by the present invention comprises a casing having a suction inlet and a delivery outlet, an impeller of a rotationally symmetric shape which is encased in the casing, and a magnet drive means disposed outside the casing coaxially to the impeller, the impeller having a rotary vane section on the outlet side and a cylindrical section equipped with a magnet means on the suction side away from the rotary vane section, and the magnet drive means being positioned so as to enclose the magnet means with the casing interposed therebetween in order to rotate the impeller around the rotation center thereof in cooperation with the magnet means, wherein at least the end section of the impeller's rotation center on the rotary vane section side is supported by a bearing.

An alternative embodiment to achieve the above-mentioned objects comprises a casing having a suction inlet and a delivery outlet, an impeller of a rotationally symmetric shape which is encased in the casing, and a magnet drive means disposed outside the casing coaxially to the impeller, the impeller having a rotary vane section wherein vanes are spaced circumferentially around the impeller and wherein the vanes incorporate permanent magnets embedded therein. The magnet drive means is positioned outside the casing and aligned with the rotary vane section in order to drive and rotate the impeller about a rotation axis, wherein the impeller forms two pivot ends which are coaxial with the rotation axis and the pivots are supported by pivot bearings.

Another alternative embodiment to achieve the above-mentioned objects comprises a casing having a suction inlet and a delivery outlet, and two gear shaped impellers of a rotationally symmetric shape which are encased in the casing and wherein the gears of the two impellers intermesh and cooperate and wherein a magnet means is disposed in one of the impellers and a magnetic drive means is positioned outside the casing and aligned with the magnet means in order to drive and rotate the impellers about a rotation axis, and further wherein each of the impellers comprises a rotation shaft at is its center and parallel to the rotation axis, each shaft having two ends which form pivots and which are supported by pivot bearings disposed in the casing.

BRIEF DESCRIPTION OF THE DRAWING

FIG. 10 shows an example of a side sectional view of another embodiment of the blood pump of the present invention.

FIG. 11 shows an example of a front view of the left side of the embodiment of FIG. 10.

DETAILED DESCRIPTION OF THE INVENTION

Figure 1:
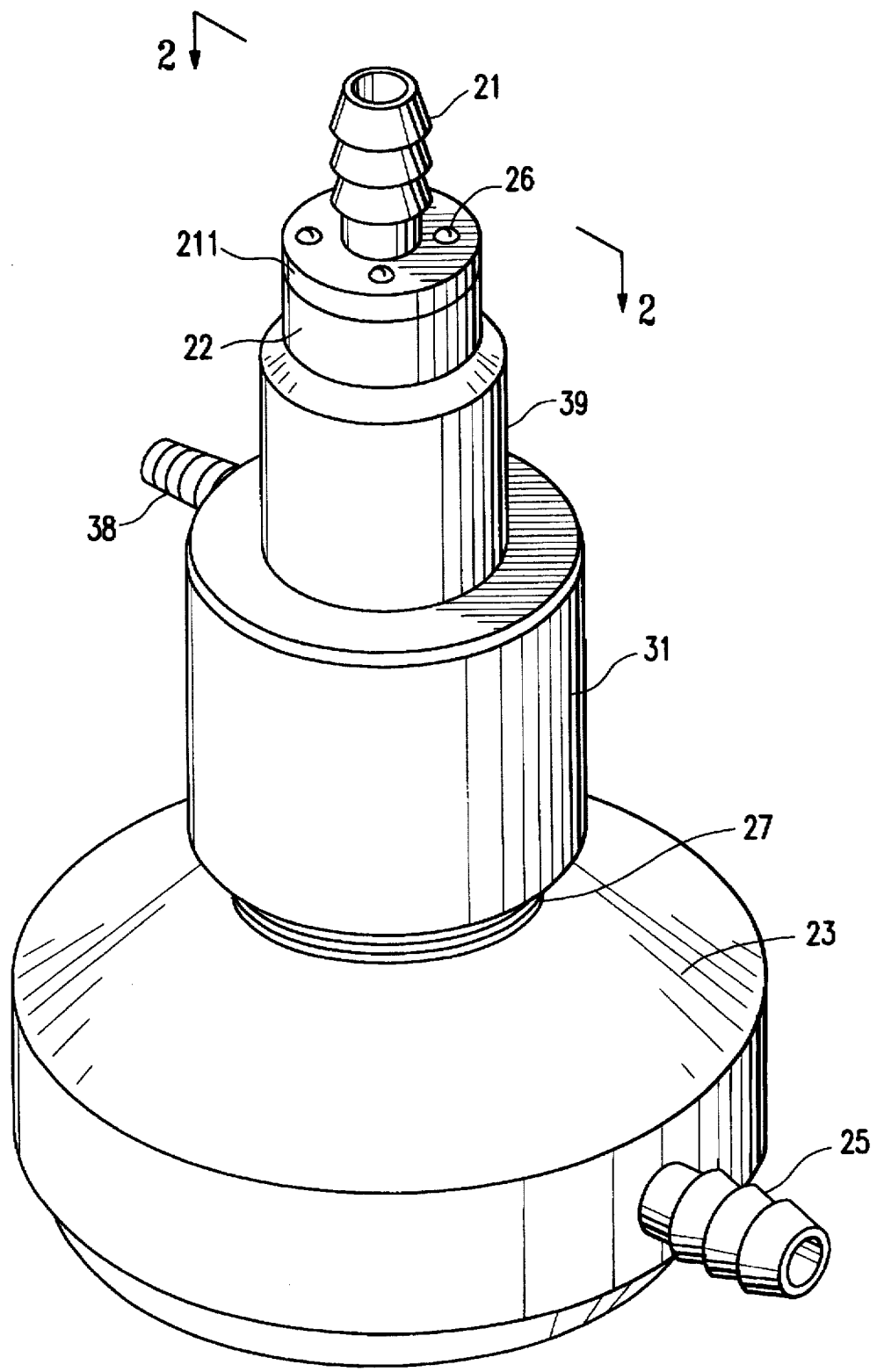
FIG. 1 shows an example of an external perspective view of an embodiment of the blood pump of the present invention.

The present invention relates to a novel centrifugal blood pump comprising a casing having a suction inlet and a delivery outlet, an impeller of a rotationally symmetric shape which is encased in the casing, and a magnet drive means disposed outside the casing coaxially to the impeller. The impeller has a rotary vane section equipped with pump vanes on the external surface thereof and a cylindrical section located on the suction inlet side away from the rotary vane section. The cylindrical section is equipped with a magnet means such as permanent magnets to magnetically rotate the impeller around the rotation center (axis) thereof in cooperation with the above-mentioned magnet drive means. The magnetic drive means is located to coaxially enclose the magnetic means of the cylindrical section of the impeller with the casing interposed therebetween. The impeller is supported by a bearing at the end of the impeller's rotation center at least on the rotary vane section side. In the preferred embodiment of the present invention, the end of the impeller's rotation center on the rotary vane section side is supported by a pivot and a pivot bearing. Both the pivot and pivot bearing included in the pivot-bearing combination are preferably made of ceramics.

When the rotationally symmetric impeller is rotated around the enter thereof, the impeller rotates stably and self-supportingly around the lower end of the rotation center by the gyroscopic function. The impeller is mainly supported by the bearing on the lower section side, that is, on the rotary vane section side and no large load is applied to the bearing on the upper section side. It is thus possible to omit the bearing at the end section of the impeller's rotation center on the impeller's top section side. However, the bearing used to support the end section can allow the impeller to rotate more stably. Either a contact-type bearing, such as a pivot bearing or a journal bearing, or a non-contact-type bearing, such as a magnet bearing, can be used as the bearing used at the upper end section. As the bearing used on the lower section side, a pivot-bearing unit can be used advantageously since the load in the radial direction of the impeller is reduced by the gyroscopic function.

The rotation of the impeller of the present invention's blood pump is further stabilized since the magnetic means and the magnetic drive means for magnetically rotating the impeller are arranged coaxially in such a manner as the relationship between the rotor and stator of a motor. In addition to the above-mentioned gyroscopic function and the coaxial arrangement of the magnetic means and the magnetic drive means, by preferably supporting the rotation center of the impeller at both the upper and lower ends of the rotation center, the rotation of the impeller can be maintained more stably. As a result, no irregular or excessive force is applied to the rotation center support sections of the impeller, thereby scarcely causing blood cell damage, that is, hemolysis.

With the blood pump of the present invention, the magnetic means mounted on the impeller is positioned at the cylindrical section on the suction inlet side, instead of the position on the rotary vane section side of the impeller, thereby allowing blood to smoothly flow through the gap between the impeller and the casing. For this reason, thrombi are rarely generated, even if the gap between the casing and the impeller's cylindrical section equipped with magnetic means such as permanent magnets is made small to increase the drive power and efficiency of the magnetic drive operation of the impeller. In other words, the blood pump of the present invention can prevent the generation of thrombi while maintaining the high efficiency of the magnetic drive operation.

Furthermore, since the magnetic means of one embodiment of the present invention is provided on the cylindrical section of the impeller instead of the position on the bottom surface side of the impeller, the gap between the bottom surface of the impeller and the bottom surface of the casing opposite thereto can be made relatively large. Accordingly, blood stagnation and excessive agitation do not occur at this gap, thereby scarcely generating thrombi and hemolysis at the pivot-bearing units or other parts. Auxiliary vanes or the like can be provided on the bottom surface of the impeller as required to enhance the flow of blood from the gap to the delivery outlet, avoiding blood stagnation at this portion. Consequently, the blood pump of the present invention scarcely generates thrombi and hemolysis and can thus be operated for an extended period of time.

The structural details and the resulting advantages of the blood pump of the present invention will be apparent from the following description of the preferred embodiments, referring to the accompanying drawings.

DETAILED DESCRIPTION OF THE PREFERRED EMBODIMENTS

Figure 2:
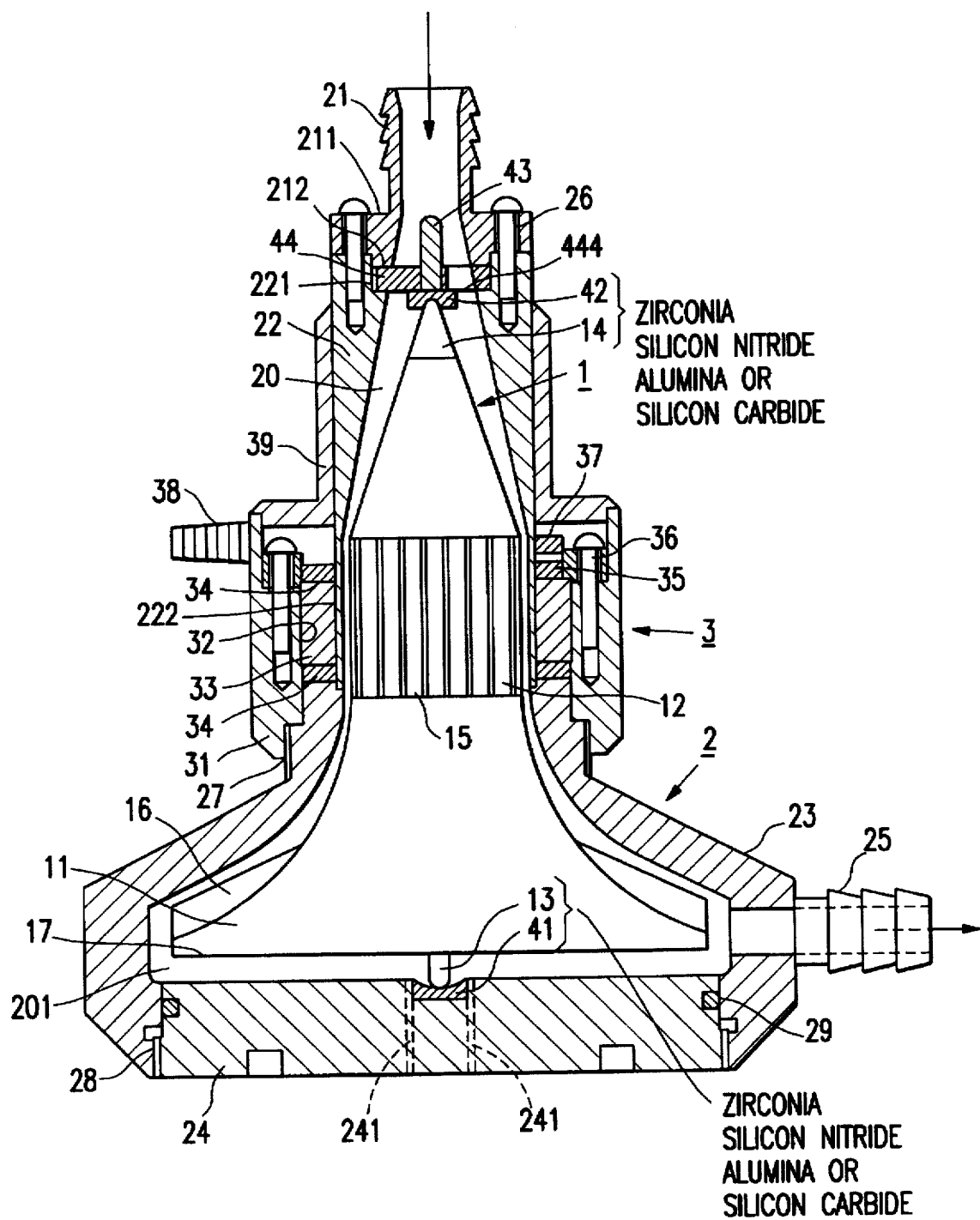
FIG. 2 shows an example of a sectional view taken along line 2—2 of FIG. 1.

FIGS. 1 and 2 show an embodiment of the centrifugal blood pump of the present invention. Numeral 1 represents an impeller rotatably accommodated in a casing 2 and having a rotationally symmetric shape. The impeller 1 is made of plastic material for example and has a rotary vane section 11 located at the impellet's lower section and a cylindrical section 12 located on the side of the suction inlet 21 away from the rotary vane section 11. At the bottom surface 17 of the impeller, a pivot 13 is disposed so that its center line aligns with the rotation center of the impeller. Also, a pivot 14 is embedded in the top section of the impeller such that the center line of the pivot aligns with the rotation center of the impeller. As the magnetic means, a group of permanent magnets 15 are arranged symmetrically along the periphery of the cylindrical section 12. Numeral 16 represents each vane. A plurality of vanes 16 are used to transfer blood to a delivery cutlet 25 by impeller rotation, thereby discharging blood from the delivery outlet 25. The cylindrical section 12 is not required to have a complete cylindrical shape, but may have a slightly tapered shape.

Figure 5:
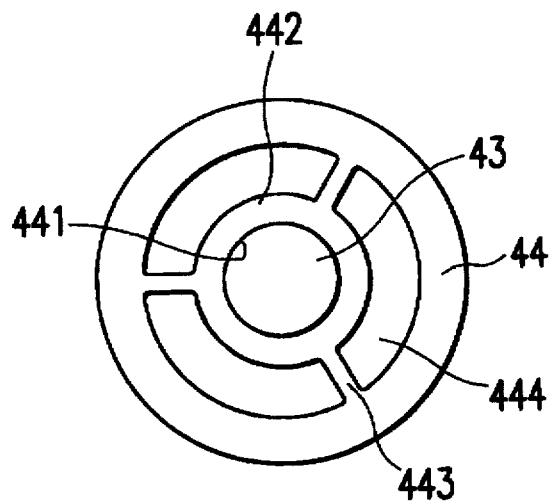
FIG. 5 shows an example of a plan view of the support section of a holding rod joined with a pivot bearing.

The casing 2 made of plastic material or the like comprises the suction inlet 21, an upper casing 22, a side casing 23 and a bottom plate 24, and rotatably accommodates the impeller 1 in the space 20 thereof. At the top section of the upper casing 22, the flange 211 of the suction inlet 21 is secured by screws 26. In addition at the top section of the upper casing 22, an annular recessed section 221 is formed. In the recessed section 221, a support ring 44 made of plastic material or the like is installed and pressed by the holding surface 212 of the flange 211 to ensure hermetical sealing between the upper casing 22 and the flange 211. The holding rod 43 joined with the bearing 42 of the pivot 14 by using an appropriate means such as adhesive is inserted into the hole 441 of the center ring 442 supported by the rib 443 of the support ring 44 and is supported by the support ring 44 as shown in FIG. 5. The blood supplied through the suction inlet 21 passes through the hole 444 of the support ring 44 and flows into the space 20 between the upper casing 22 and the impeller 1.

The cylindrical section 222 at the lower section of the upper casing 22 is made thinner than other sections to reduce the gap between the permanent magnets 15 and a coil 34 described later. The lower end section of the upper casing 22 is hermetically connected to the upper end section of the side casing 23 by an appropriate method such as welding. To the inner surface of the side casing 23 on the lower end side thereof, the bottom plate 24 is secured by a screw 28 so that the bearing 41 embedded in the center of the upper surface of the bottom plate 24 can properly contact the pivot 13, so that the pivot 14 can properly contact the bearing 42 and so that the bottom plate 24 can be positioned vertically by screwing movement. Numeral 29 represents an O-ring used to hermetically seal the connection of the side casing 22 and the bottom plate 24. The side casing 23 has the delivery outlet 25 just above the connection section of the side casing 23 and the bottom plate 24. The delivery outlet 25 is disposed to extend in the direction tangential or nearly tangential to the rotation direction of the impeller 1 and on the tangential side of the rotation direction.

The magnetic drive means 3 disposed outside the casing 2 is described below. In the inner surface of the side wall 31 contacted to the side casing 23 by a screw 27, a magnetic core 33 with the coil 34 wound thereon is fitted in the annular recessed section 32 disposed coaxially to the cylindrical section 222 of the upper casing 22. The magnetic core 33 is secured and fixed via a holding member 35 by screws 36. The coil 34 and the magnetic core 33 are disposed so that they nearly contact the cylindrical section 222 of the casing 22. With this structure, the coil 34 coaxially encloses the permanent magnets 15 installed in the impeller 1 so that the thin cylindrical section 222 of the upper casing 22 is interposed therebetween. When the coil 34 is actuated, the impeller 1 is rotated by the mutual action of the coil 34 for generating a rotating magnetic field and the permanent magnets 15. The magnetic drive means 3 and the impeller's cylindrical section 12 equipped with the magnetic means may be the stator and rotor of a brushless DC motor respectively.

According to the results of the experiments conducted by the inventors of the present invention, the gap between the cylindrical section 222 of the casing 22 and the impeller's cylindrical section 12 equipped with the permanent magnets 15 is preferably determined in the range of 0.5 to 3.0 mm. If the gap is smaller than 0.5 mm, thrombi are apt to be generated and pressure loss increases. If the gap exceeds 3.0, magnetic drive force and the efficiency of the pump decrease. Even when the above-mentioned gap exceeds 3 mm, sufficient drive force can be obtained if the magnetic force generated by the coil 34 is made greater. In this case, however, the coil 34 must be made larger.

Figure 9:
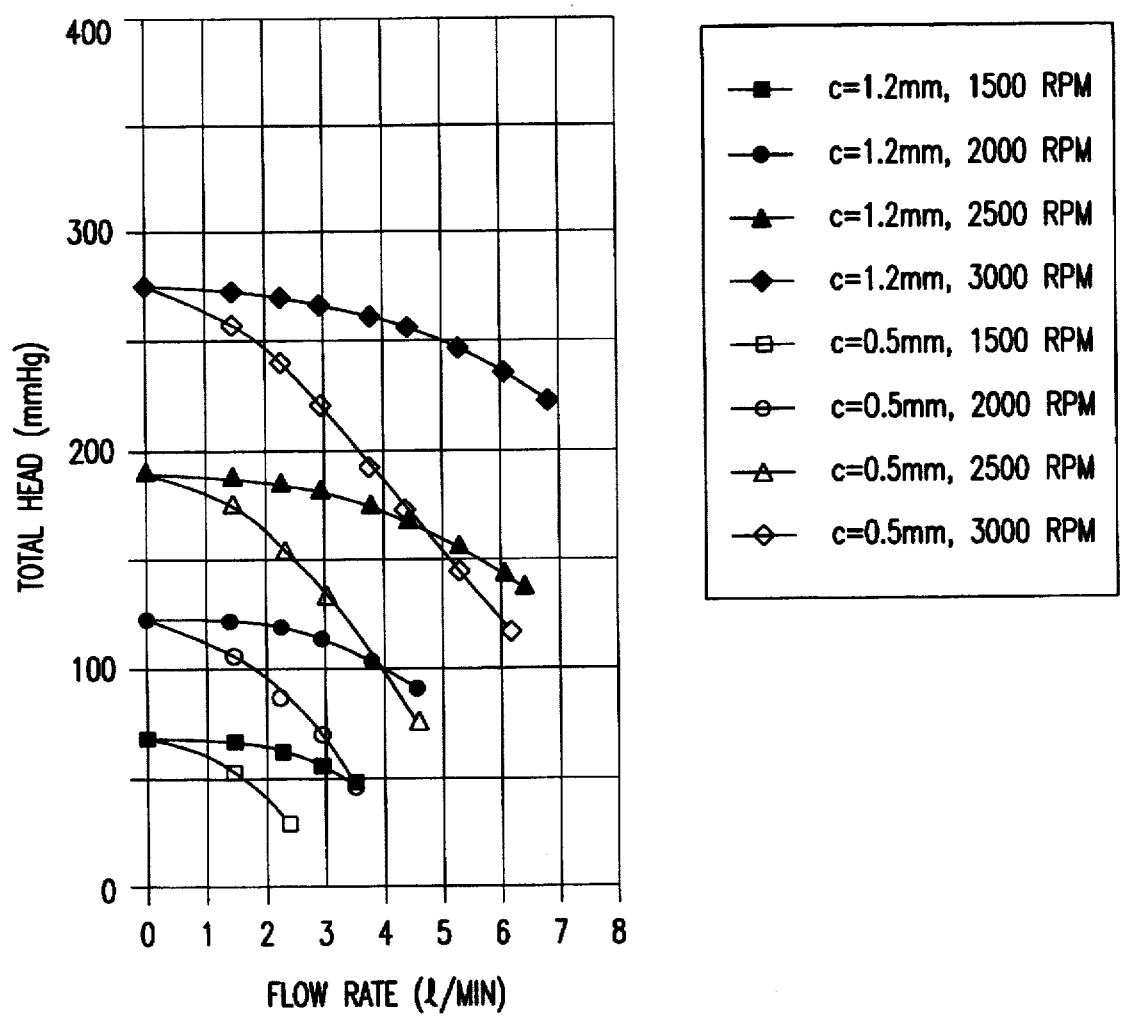
FIG. 9 shows an example of a graph illustrating the performance curve of the blood pump of the present invention.

FIG. 9 shows the relationship between the flow rate of blood and the delivery pressure in the case of the blood pump of the present invention at various rotation speeds, with the above-mentioned gap C set at 0.5 or 1.2 mm. According to this graph, it is understood that the blood pump of the present invention has a sufficient capability for transferring blood by pressure.

As the magnetic drive means, a group of permanent magnets can be arranged, disposed and rotated by a motor, instead of generating a rotating magnetic field using a coil. In this case, the above mentioned gap is preferably in the range of 0.5 to 10 mm, since strong magnets can be used for the permanent magnets arranged and disposed outside the casing. With the blood pump of the present invention, the unit comprising the casing 2 and the impeller 1 is made disposable and the magnetic drive means 3 is used repeatedly. It is therefore advantageous that the permanent magnets arranged and disposed outside the casing are composed of strong magnets and that the permanent magnets mounted on the impeller are composed of cheap magnets. The magnetic drive means incorporating permanent magnets, instead of the coil 34, can be provided as an auxiliary magnetic drive means in case of power failure, since the permanent magnets can be rotated by hand.

Referring to FIG. 2, numeral 37 represents a Hall sensor used to detect the gap between the impeller's permanent magnets and the casing, and the position and the rotation speed of the impeller. Numeral 38 represents the input/output ports for lead wires (not shown). Numeral 39 represents a cover set in or secured by screws to the upper end of the side wall 31 of the magnetic drive means 3. Since the disposable unit comprising the casing 2 and the impeller 1 is connected to the magnetic drive means 3 only by the screw 27, the disposable unit can be attached to or detached from the magnetic drive means 3 by engaging or disengaging the screw 27.

Figure 4:
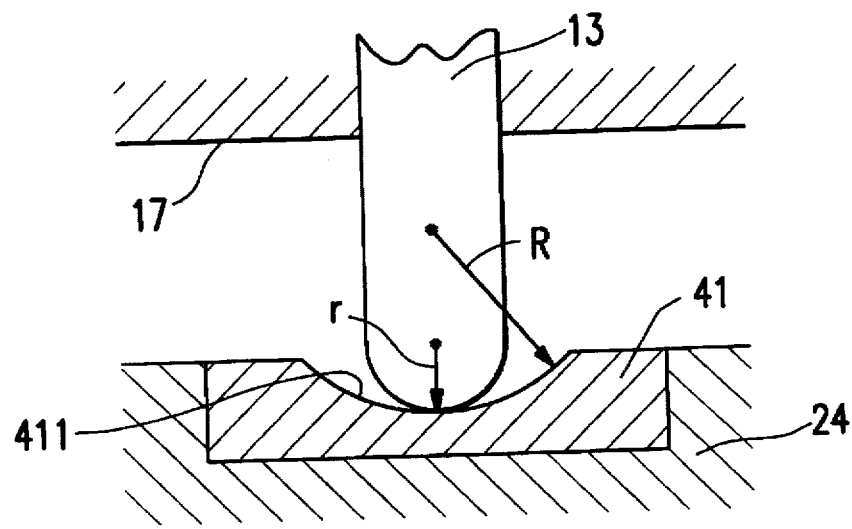
FIG. 4 shows an example of an enlarged sectional view of a pivot bearing.

According to the experiments, conducted by the inventors of the present invention, regarding the pivot 13 and the bearing 41 thereof located on the lower section side of the impeller and the pivot 14 and the bearing 42 thereof located on the upper section side of the impeller, ceramics are superior to metals and plastic materials in resistance against thrombus generation and thus rarely generate thrombi. In addition, ceramics are highly resistant against friction. For these reasons, at least the pivot or the bearing of each of these pivot-bearing combinations is desired to be made of ceramics such as alumina, zirconia, silicon carbide or silicon nitride. These ceramics may be a combination of any of the aforementioned materials. In particular, since silicon carbide is high in heat conductivity, it is apt to easily dissipate friction heat. Furthermore, since silicon carbide contains carbon, it is superior in sliding performance. For these reasons, silicon carbide is best suited. As such, one embodiment may have a ceramic which contains not less than 85 weight % silicon carbide. Alumina is also suited for practical applications since it is low in cost and relatively high in heat conductivity. As such, another embodiment may have a ceramic which contains not less than 85 weight % alumina. Regarding the radius of curvature r at the leading end of the pivot 13 and the radius of curvature R at the recessed curved surface 411 of the bearing 41 as shown in FIG. 4, the ratio of R/r is preferred in the range of 1 to 4. If the ratio exceeds 4, the support of the pivot by the bearing becomes unstable. The range of 2 to 4 is further desirable, since it has been confirmed by experiments that hemolysis occurs far scarcely when the ratio is 2 or more.

As described above, since no large load is applied to the end section of the impeller's rotation center on the impeller's top section side because of the gyroscopic function, the bearing used at the end section is not limited to a pivot bearing, but a variety of types of bearings including non-contact type bearings can be used suitably. In some cases, the impeller can be used without being supported by the bearing at the top end section. Although in the pump as shown in FIG. 2 at the end section of the impeller's rotation center on the impeller's top section side and on the rotary vane side, pivots 14 and 13 are embedded in the impeller, it is of course possible that the rotation center can have a shape of a single shaft extending from the top end to the lower end.

Figure 8:
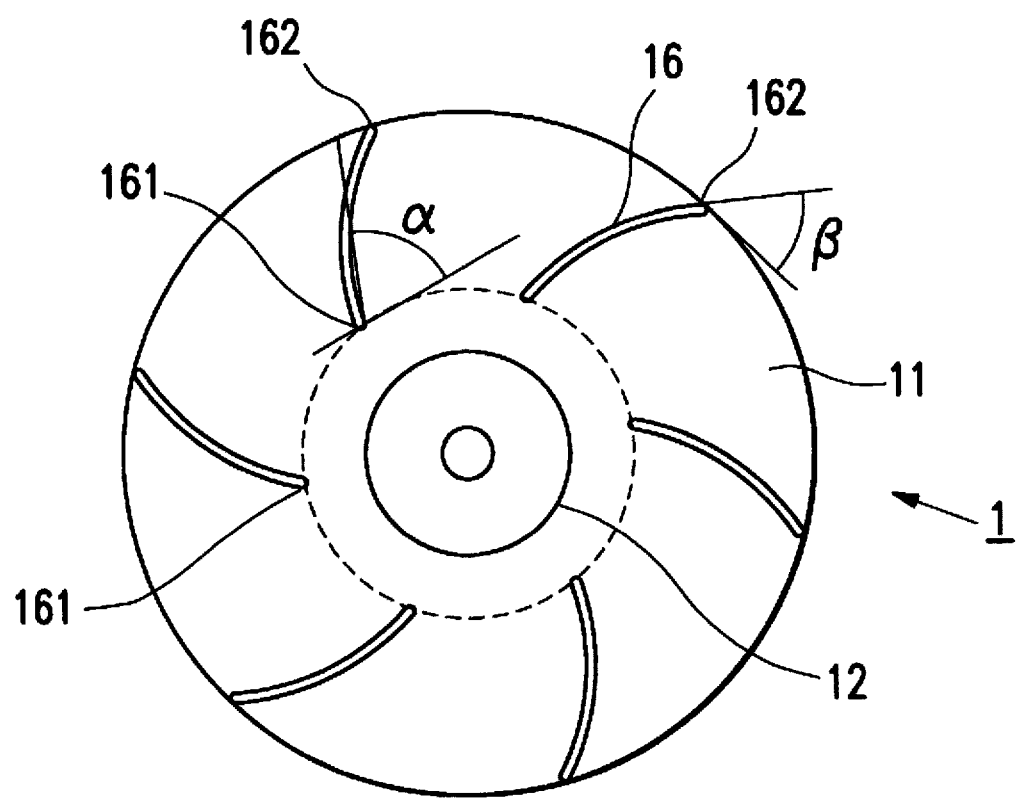
FIG. 8 shows an example of a plan view of the impeller illustrating the entrance and exit angles of the impeller's vanes.

The vanes 16 of the impeller 1 can have a variety of shapes, such as a curved or straight shape, as long as the vanes offer pumping functions. However, according to the results of the experiments conducted by the inventors of the present invention, hemolysis occurs far scarcely when the entrance angle α of the vane is in the range of 10 to 70 degrees and the exit angle β of the vane is in the range of 50 to 70 degrees. It is therefore desirable to determine the entrance and exit angles of the vane in the above mentioned ranges. As shown in FIG. 8 (indicating curved vanes), the above-mentioned entrance angle α is an angle formed by the tangent line of the circle obtained by connecting the leading ends 161 of the vanes 16 on the blood entrance sides and the tangent line at the blood entrance end of each vane, and the above-mentioned exit angle β is an angle formed by the tangent line at the blood exit end 162 of each vane and the tangent line of the external circle of the impeller's lower end section at the exit end 162 of each vane.

Figure 3:
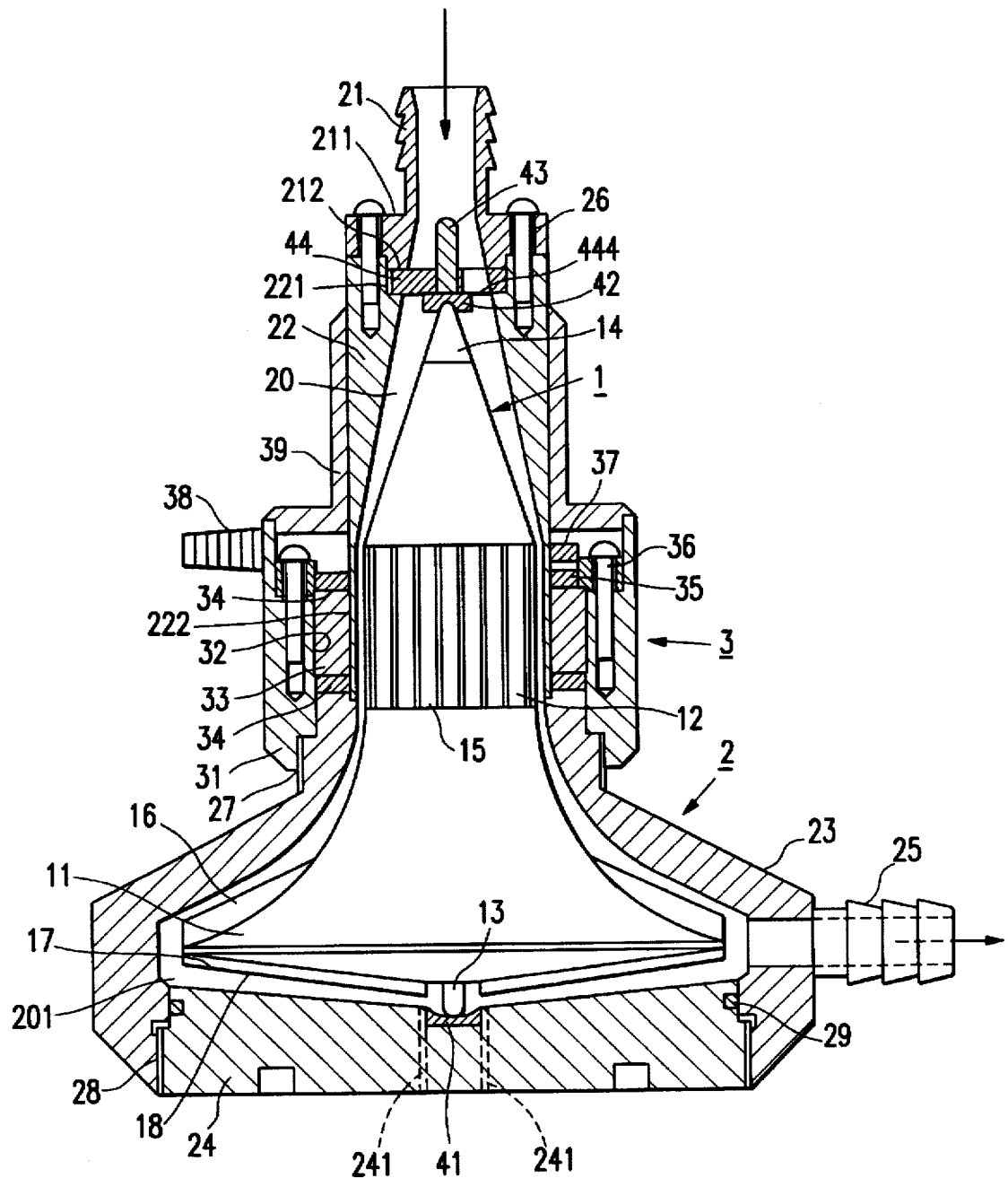
FIG. 3 shows an example of a longitudinal sectional view of another embodiment of the blood pump of the present invention.
Figure 6:
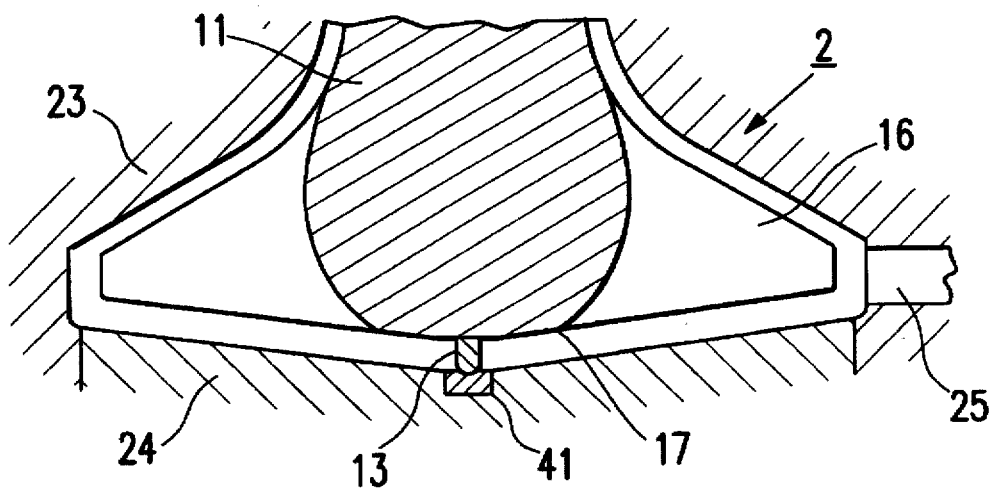
FIGS. 6 and 7 are sectional views illustrating other structures of the rotary vane section of the impeller.
Figure 7:
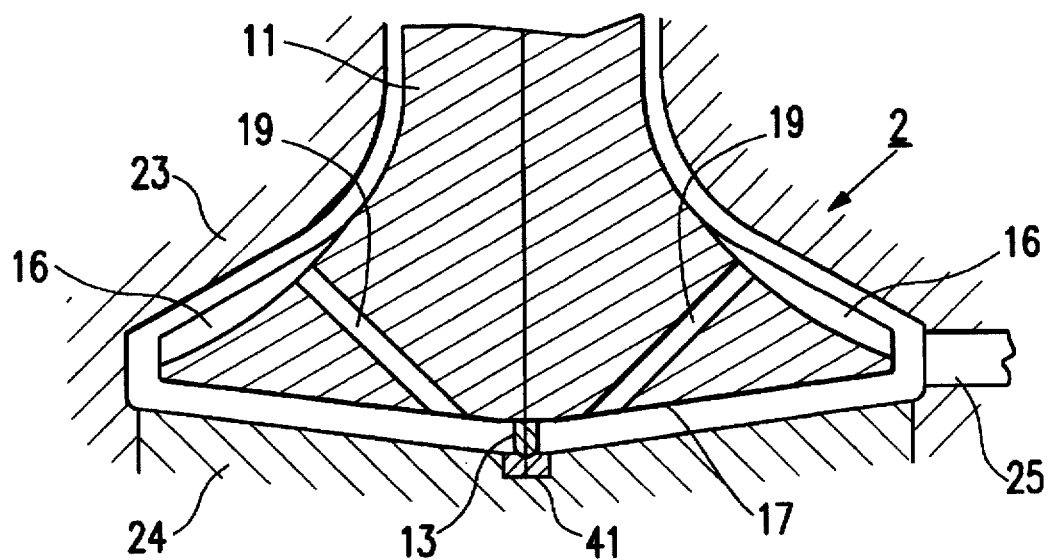

With the present invention, auxiliary vanes can be provided on the bottom surface 17 of the impeller 1 to allow the blood flowed into the space 201 between the bottom surface 17 of the impeller 1 and the casing 2 to be transferred to the delivery outlet 25, and to eliminate stagnation in the space, thereby preventing the generation of thrombi. FIG. 3 shows the cross section of an embodiment equipped with such auxiliary vanes. The generation of thrombi can further be prevented by providing water purging through holes 241 around the bearing 41 of the bottom plate 24 as shown by the broken lines in FIG. 3 and supplying a mixture liquid from the outside comprising a physiological saline solution and a blood anti-coagulation agent or a thrombus dissolution agent. More suitable results are obtained by providing porous elements inside the through holes 241 so that the supplied liquid can seep through the porous elements, or by forming the bearing 41 by using a porous element having lots of micro pores with the sizes ranging from 60A to several millimeters so that the supplied liquid can seep through the bearing 41. The same reference numerals used in FIGS. 2 and 3 represent the same corresponding elements. The embodiment shown in FIG. 3 is the same as that shown in FIG. 2 except for the shapes of the bottom surface 17 of the impeller 1 and the bottom plate 24 of the casing 2 and except that the auxiliary vanes 18 and the water purging through holes 241 are provided. FIGS. 6 and 7 show embodiments which enhance the flow of the blood located in the space between the bottom surface 17 of the impeller 1 and the bottom plate 24 of the casing 2 to prevent the generation of thrombi. The rotary vane section 11 shown in FIG. 6 is an open type. The rotary vane section 11 shown in FIG. 7 is equipped with through holes 19 which pass from the external surface of the rotary vane section 11 to positions close to the pivot 13 of the bottom surface 17.

A further embodiment is illustrated in FIGS. 10 and 11 and will now be described. The blood pump of this embodiment has a casing 100. Casing 100 is of a cylindrical shape in a preferred embodiment. Disposed within the casing 100 are support bars 101 and 102. Support bars 101 and 102 rotatably support a column shaped impeller 103. Impeller 103 is rotatable around an axis X. Pivots 104 and 105 are disposed at each end of impeller 103. Support bars 101 and 102 each incorporate a pivot bearing 106 and 107, respectively. The pivot bearings 106 and 107 cooperate with pivots 104 and 105 to rotatably support impeller 103. Further, the impeller 103 is equipped with vanes 108. Vanes 108 act to force a material, such as blood, through the casing 100. Each vane 108 may have a permanent magnet 109 embedded therein. These magnets 109 work in cooperation with an external magnetic drive means 110. The drive means 110 are positioned outside the casing 100 and aligned with the vanes 108. The magnetic drive means 110 may be a brushless stator or coupling magnet.

In operation, the magnetic drive means 110 works in conjunction with the permanent magnets 109 embedded in vanes 108 to rotate impeller 103, for example in a direction indicated by arrow 111. As the impeller rotates, a material such as blood, is drawn in through an inlet port 112 and forced through the casing 100 and out through an outlet port 113.

With regard to the pivots 104 and 105 and the pivot bearings 106 and 107, it is desirable that both the pivots and the pivot bearings are made of a ceramic. However, it is also within the scope of the present invention that either the pivots or the pivot bearings are made of a ceramic and the others are made of metal, such as a titanium alloy, for example. Further, it is also an alternative to have the pivots or the pivot bearings made of metal but coated with a ceramic on the surface of the metal. Furthermore, it is another alternative to have the pivots or the pivot bearings made of either metal or a ceramic and coated with diamond on the surface thereof. Also, the pivot bearings can be fixed to the casing through a resilient material so that the pivots may always be pressed. In this way, even as the pivots experience wear, generation of a gap between the pivots and the pivot bearings can be avoided. To obtain pivots or pivot bearings which are hard to break and are superior in wear resistance, a preferred embodiment will use ceramics having the following characteristics: a bending strength of 400 MPa or more, a Vickers hardness (Hv) of 1000 kg/mm$^2$ or more, a Young's modulus of 200 GPa or more, an average thermal expansion coefficient at 40°–400° C. of $15 \times 10^{-6}$/°C. or less, and wherein the content of precious metal harmful to the living body is: 0.1 weight % or less. Further the radius of curvature at the end of the pivot is desired to be 0.5 mm or more.

Still another embodiment of the present invention is explained next referring to FIGS. 16 and 17. The same numerals as those used in the previous figures represent the corresponding parts. The impeller of this embodiment is supported by the casing 3 via pivots 21, 23 and pivot bearings 22, 24 at both the upper and lower ends of the rotation center axis thereof. The pivot 21 formed at the lower end of the rotation shaft 19 of the impeller 1 is supported by a bearing 22, a watch-type jewelled bearing, disposed at the center of the bottom plate 33 of the casing 3. The pivot 23 formed at the upper end of the above-mentioned rotation shaft is supported by a pivot bearing 24, which is similar to the bearing 22, embeddedly disposed at the top section 311 of the conical section 31 of the casing 3. The inlet port 34 of the casing 3 extends parallel to the center line of the Conical section at a position eccentric from the top section 311 of the conical section 31 of the casing 3. More particularly, the inlet port 34 is disposed so that the center axis thereof is positioned 5 mm away from the center line of the conical section of the casing in parallel to the center line. Furthermore, in this embodiment, auxiliary vanes 25 are disposed on the bottom surface 12 of the impeller 1 to prevent the generation of thrombus which is apt to occur because of the stagnation of blood around the pivot 21 and the pivot bearing 22 at the lower end of the rotation shaft 19 of the impeller 1. The generation of thrombus can be prevented more effectively by disposing water-purging through holes (not shown) around the bearing 22 which in one embodiment may be provided on the bottom plate 33 of the casing 3 and by supplying mixture liquid of physiological saline solution, anticoagulant and thrombolytic agent vis the through holes from outside the pump, although the through holes are not shown in the figures. Moreover, in this embodiment, the frame 44 of the magnet drive means 4 is threadedly engaged with the bottom plate 33 of the casing via a thread 54 so that the magnet drive means 4 is removably installed in the casing 3. Accordingly, although the casing 3 and the impeller 1 can be thrown away, the magnet drive means 4 can be used repeatedly.

In the two pairs of the pivots and the pivot bearings disposed at the upper and lower ends of the rotation shaft 19 of the impeller 1, at least one part of each pair in one embodiment is preferably made of ceramics, such alumina, zirconia, silicon carbide or silicon nitride, being superior in resistance against thrombus and friction.

Since both the upper and lower ends of the rotation shaft 19 of the impeller 1 used in this embodiment are supported by bearings 22, 24, the rotation of the impeller 1 is smooth and stable. In addition, since the bearing 24 of the pivot 23 is disposed in the wall of the top section of the conical section of the casing 3, no supporting means is necessary to support the bearing. Furthermore, since the inlet port 34 is disposed eccentric from the top section of the conical section as described above, blood sucked from the inlet port 34 does not directly collide against the pivot 23 and the bearing 24, and the flow of the blood is not disturbed by these parts. Consequently, in the case of this embodiment of the blood pump of the present invention, the generation of hemolysis and thrombus can also be prevented at the supporting section on the upper end side of the rotation shaft 19 of the impeller 1, thereby enabling the embodiment to be operated continuously for an extended period of time.

Figure 16:
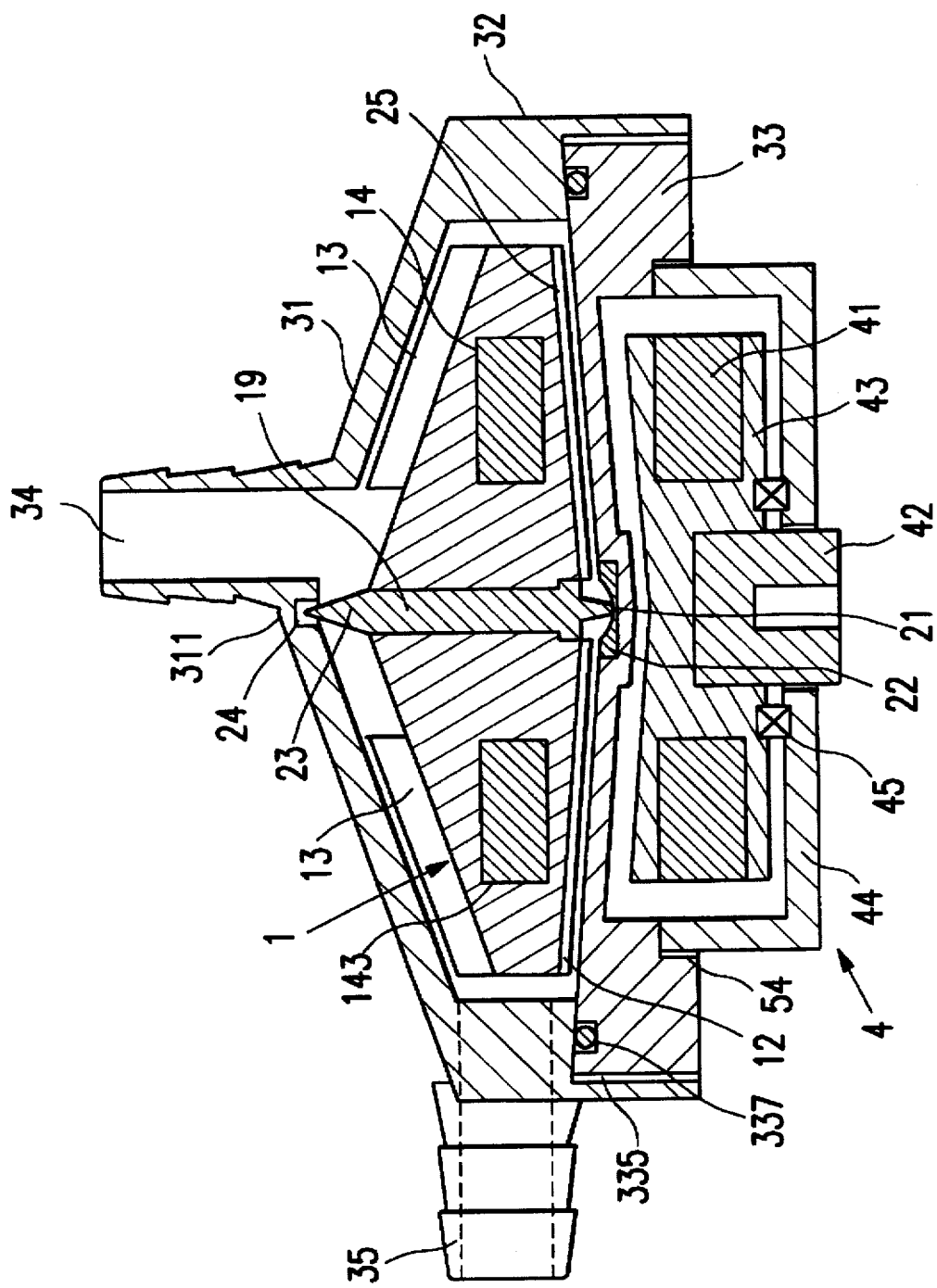
FIGS. 16 and 17 are a vertical sectional view and a top plan view respectively illustrating still another embodiment of the blood pump of the present invention.
Figure 17:
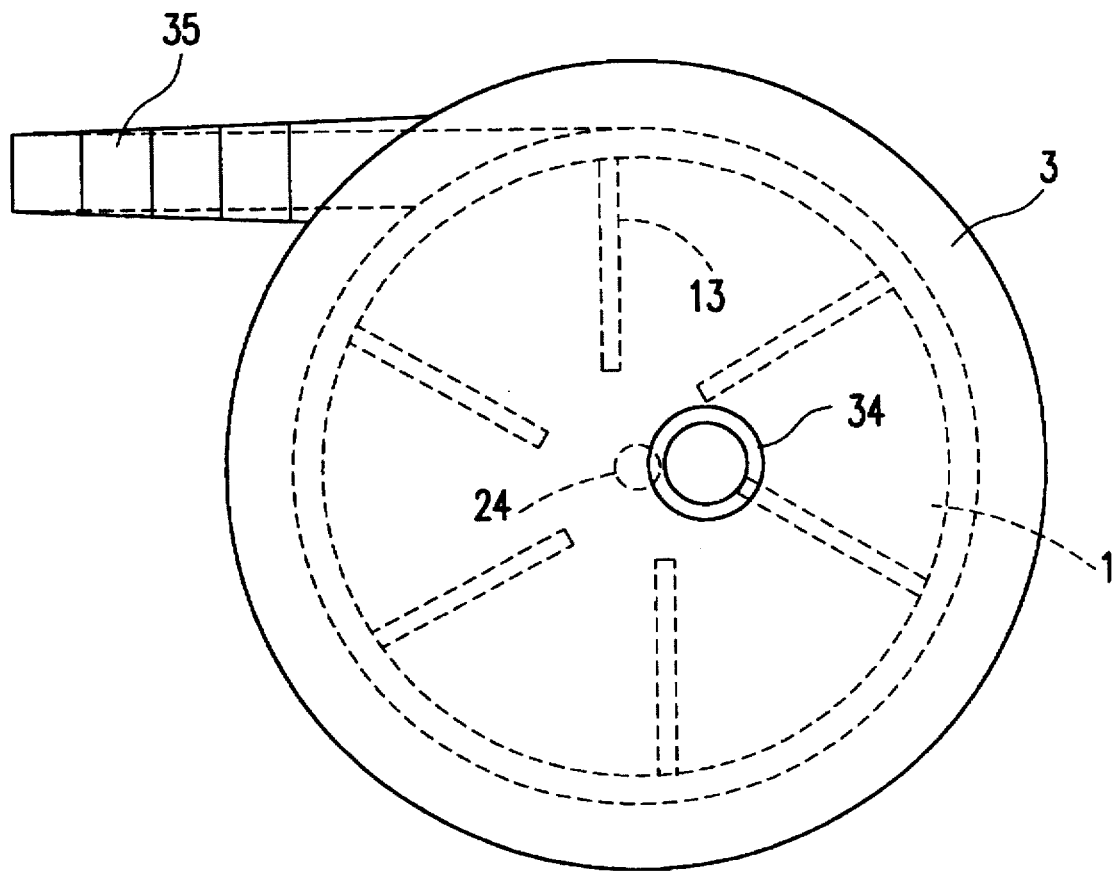
Figure 18:
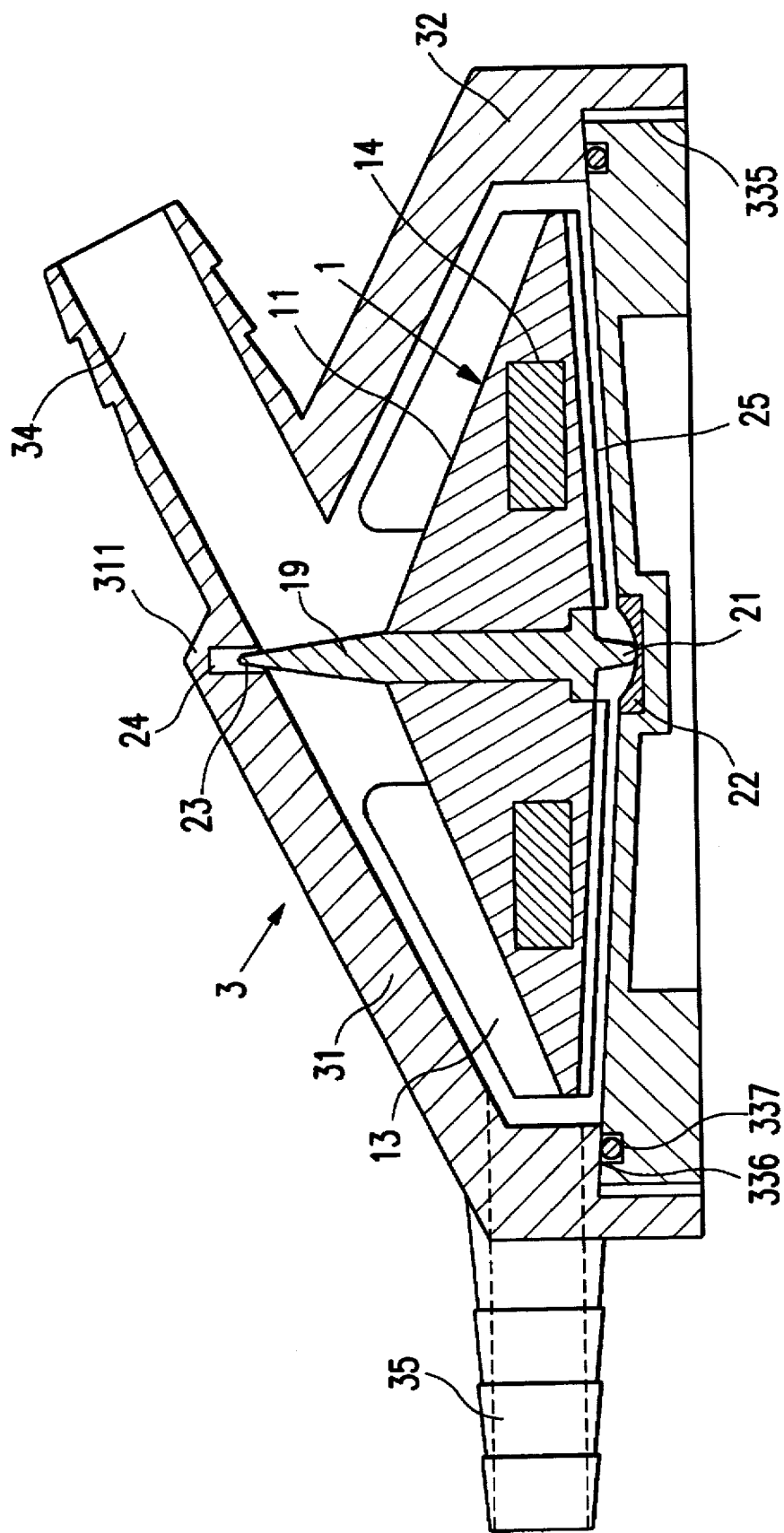
FIGS. 18 and 19 are a vertical sectional view and a top plan view respectively illustrating yet still another embodiment of the blood pump of the present invention.
Figure 19:
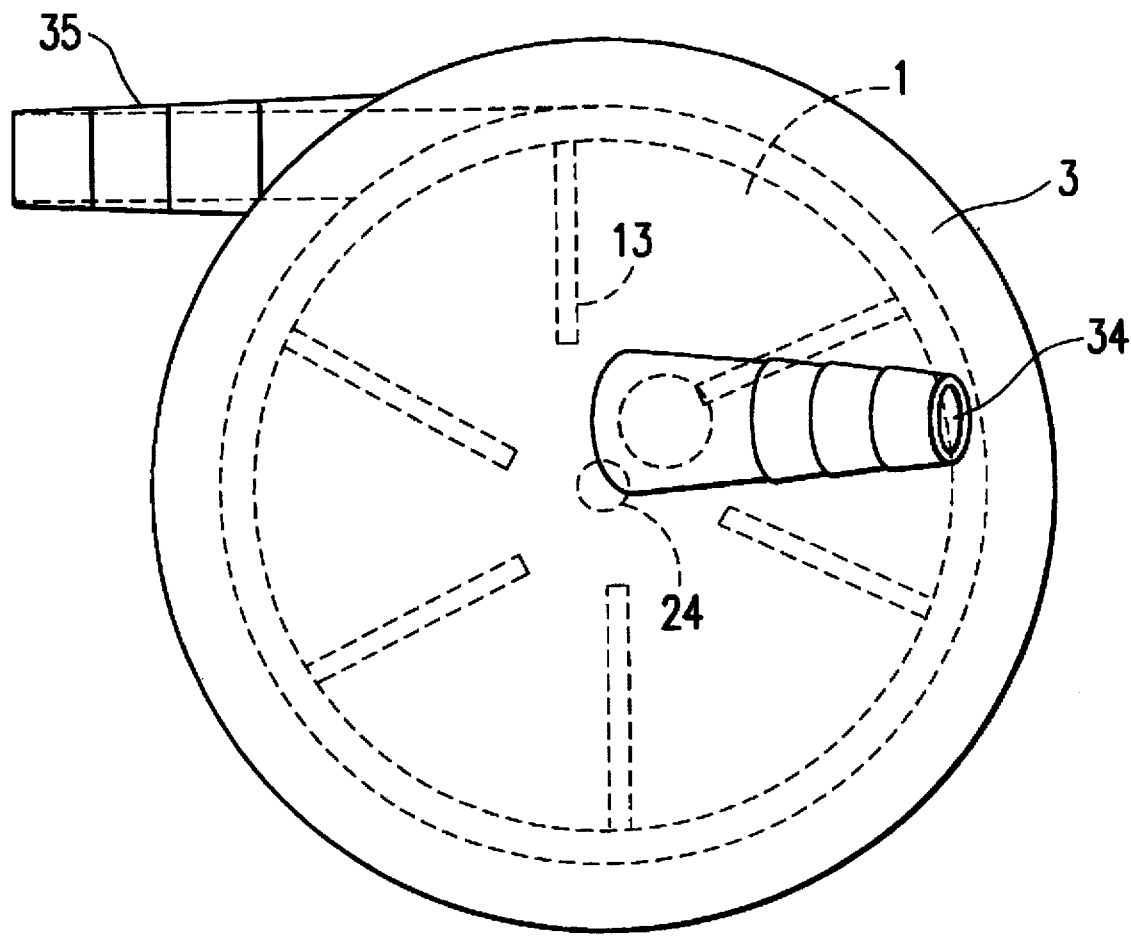

FIGS. 18 and 19 show yet another embodiment wherein the extension direction of the inlet port described in the above-mentioned embodiment shown in FIGS. 16 and 17 is changed. In this embodiment, the inlet port 34 is positioned eccentric from the top section of the conical section and extends in an inclined direction instead of the direction parallel to the center line of the conical section. Except for the inclined inlet port 34, this embodiment is the same as the embodiment of the blood pump shown in FIGS. 16 and 17. (FIGS. 18 and 19, however, show a condition wherein the magnet drive means 4 is removed.) Accordingly, in this embodiment of the blood pump of the present invention, the rotation of the impeller 1 is smooth and stable, and the generation of hemolysis and thrombus is prevented around the pivot and the pivot bearing 24 at the upper end of the rotation shaft 19 of the impeller 1. Moreover, since the angle between the inclined extension direction of the inlet port 34 and the direction of the outlet port 35 of this embodiment of the blood pump can be set at any value in the range of 3600 or less, the blood pump can be embedded at any position. When this blood pump is used for external blood circulation or heart-lung machines, it is advantageous in that the pump can be easily built in a variety of circuits.

Figure 14:
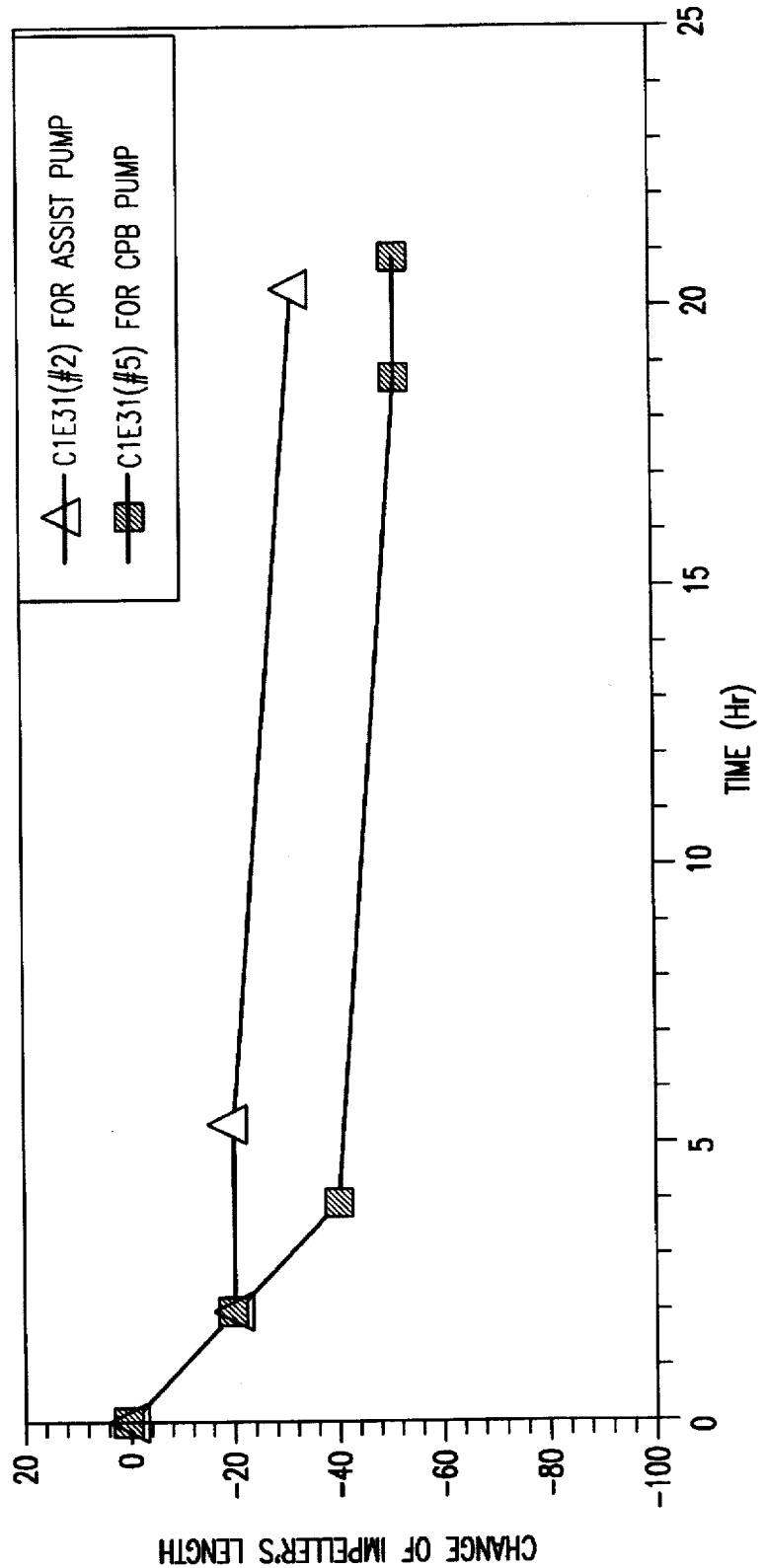
FIG. 14 shows an example of a graph illustrating wear resistance of an impeller of the present invention.

The pump described directly above was made and tested having pivot and pivot bearings made of silicon carbide ceramics and used for assist pumps and CPB pumps. FIG. 14 illustrates the relationship between the operation time and the change in pivot length (amount of wear) obtained as the results of measurements. As illustrated in FIG. 14, a considerable amount of wear was detected for the first several hours of operation. After that period, however, the amount of wear was negligible. Even after 20 hours of operation, the amount of wear was only about several tens of micrometers. In comparison, when a pivot made of metal (such as stainless steel) was used under the same conditions, the amount of wear of the pivot reached 300 micrometers after several hours of operation (this data is not shown in FIG. 14).

Figure 15:
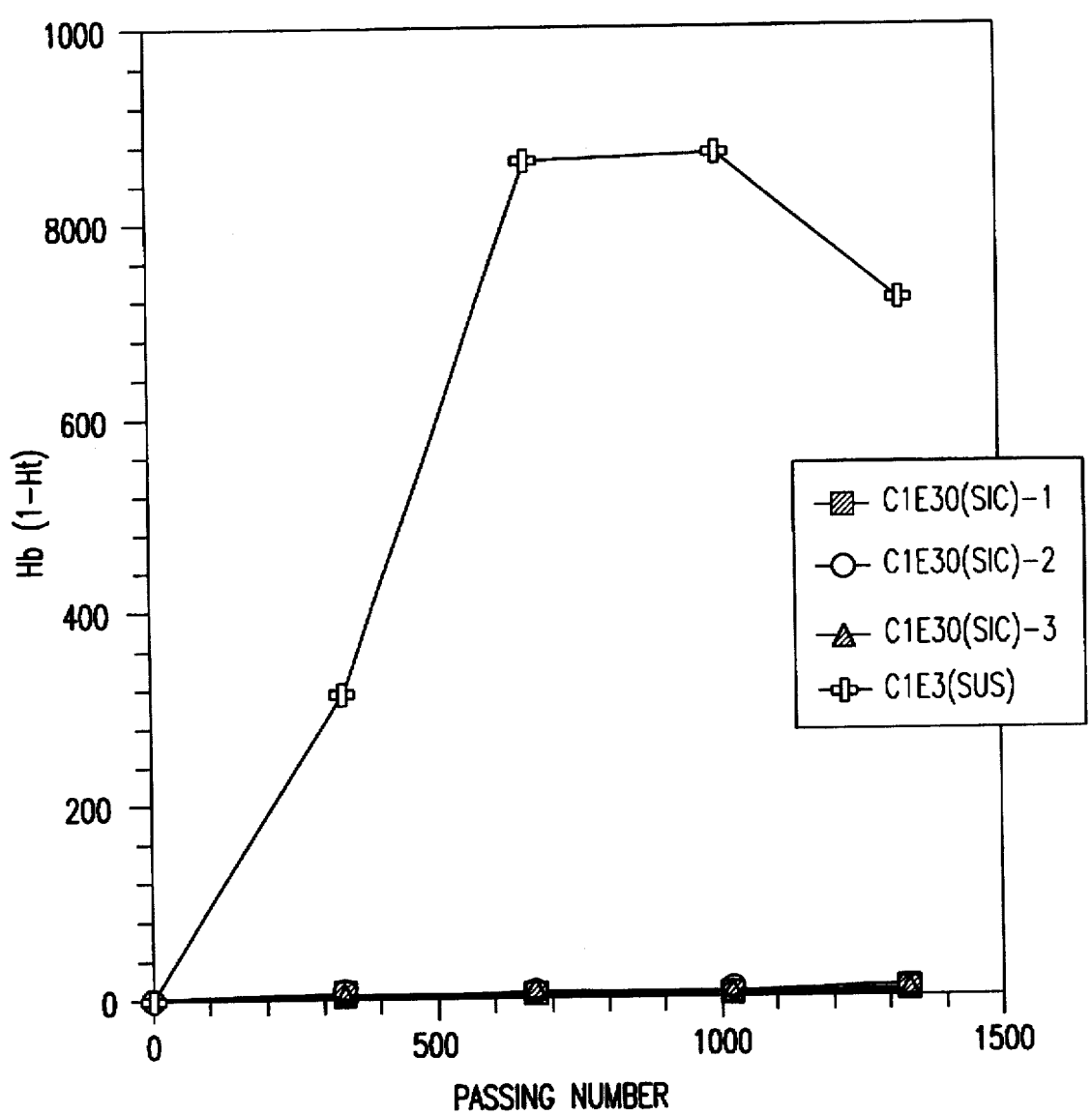
FIG. 15 shows an example of a graph illustrating hemolytic characteristics of the present invention.

Additionally, measurements of hemolytic characteristics were also taken during the experiments described above and are illustrated in FIG. 15. The relationship between operation time and the hemolytic characteristic of pivots was measured by using pivots made of ceramics (silicon carbide), and pivots made of metal (stainless steel). HB (1-Ht), which is measured along the vertical axis in FIG. 15, is an index used to indicate the hemolytic characteristic. The higher the index value, the greater the hemolytic characteristic. As the results illustrated in FIG. 15 indicate, it is clearly shown that the hemolytic characteristic of ceramic pivots is very low in comparison to that of stainless steel pivots. The plot lines for C1E30-1, C1E30-2 and C1E30-3 represent pivots using silicon carbide ceramics and the C1E3 plot line represents a pivot using stainless steel. It is to be assumed that when a metal pivot is used the rotation conditions of the impeller are changed by a large amount of wear caused in the metal pivot, thereby being likely to cause hemolysis.

The ceramic pivots and pivot bearings are highly resistant to thrombus generation. Although no data is available, ceramic pivots hardly generate thrombi because of the following reasons: (a) the ceramic surface is apt to become wet with water, since the angle of contact with water is small, (generally speaking, materials having good wettability with water are superior in the anti-thrombogenic characteristic; (b) since newly exposed ceramic surfaces generated by wear are low in chemical activity, thrombus formation is not accelerated; (c) since ceramic surfaces do not have projections, but have recesses, such as pores and grooves, red corpuscles, white corpuscles, blood platelets, etc. are hardly trapped, thereby preventing thrombi; (d) ceramic powder generated by wear hardly acts as a starting point for thrombus generation.

Figure 13:
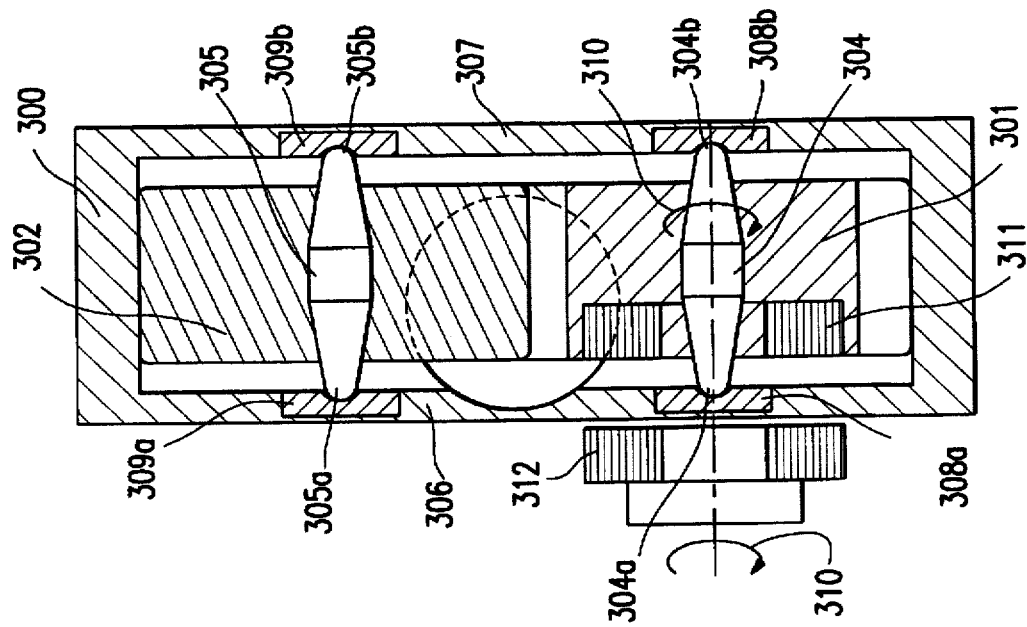
FIG. 13 shows an example of a front sectional view of the embodiment of FIG. 12.
Figure 12:
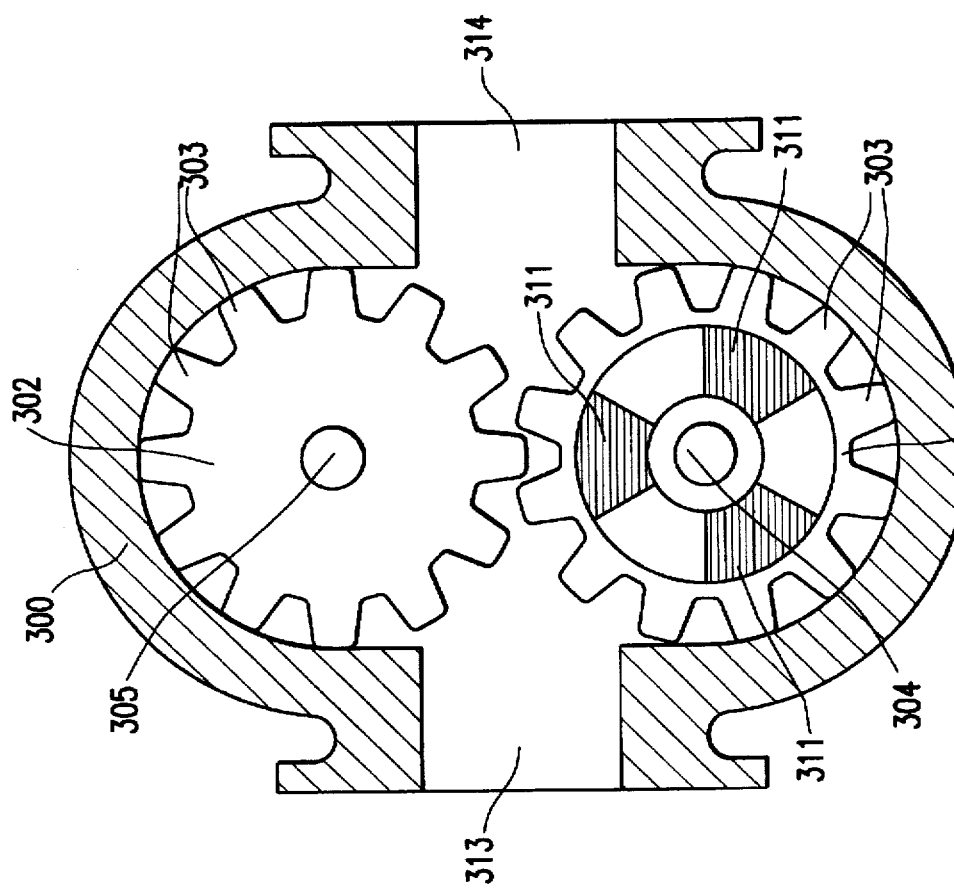
FIG. 12 shows a side sectional view of another embodiment of the blood pump of the present invention.

A further embodiment of the present invention is illustrated in FIGS. 12 and 13 and will be described hereinafter. The blood pump of this embodiment has a casing 300. The casing 300 houses impellers 301 and 302. Impellers 301 and 302 are formed with gears 303 integral with the outside surface of the impellers 301 and 302. The gears 303 of impellers 301 and 302 mesh together as is illustrated in FIG. 12. Impellers 301 and 302 further comprise shafts 304 and 305, respectively. Impellers 301 and 302 are rotatable about shafts 304 and 305, respectively. Shafts 304 and 305 are made of ceramics in a preferred embodiment. Shafts 304 and 305 have ends 304a and 304b and 305a and 305b, respectively, which form pivots. Casing 300 comprises casing walls 306 and 307. Casing walls 306 and 307 comprise pivot bearings 308a and 308b which rotatably support shaft 304 at pivots 304a and 304b and pivot bearings 309a and 309b which rotatably support shaft 305 at pivots 305a and 305b, as illustrated in FIG. 13. Pivot bearings 308a, 308b, 309a and 309b are made of ceramics in a preferred embodiment. Pivots 304a, 304b, 305a and 305b cooperate with pivot bearings 308a, 308b, 309a and 309b, respectively permit rotation of impellers 301 and 302 in a direction indicated by arrows 310. Further, impeller 301 comprises magnet means 311 such as a plurality of circumferentially spaced permanent magnets. Further, there is a magnetic drive means 312 such as a brushless motor stator or coupling magnet which is disposed outside the casing 300 and aligned with impeller 301 and magnet means 312. The magnetic drive means 311, in cooperation with magnet means 311, drives impeller 301. The gears of impeller 301 engage impeller 302, as illustrated in FIG. 12, and therefore when impeller 301 is driven and thereby rotated by magnetic drive means 312, impeller 302 is also driven and thereby rotated, each impeller rotating about its respective support shaft.

In operation, magnetic drive means 312 and permanent magnet 311 act in cooperation to drive and rotate impeller 301 in a direction indicated by arrows 310. As impeller 301 is rotated so is impeller 302. As both impellers 301 and 302 rotate blood is drawn in through the inlet 313 and driven out through outlet 314.

The discussion regarding the pivots and pivot bearings, the use of ceramics for the pivots and pivot bearings and the experimental data detailing the ceramic pivots in relation to the embodiment illustrated in FIGS. 10 and 11 are also applicable to the pivots and pivot bearings of the embodiment illustrated in FIGS. 12 and 13.

Although the present invention has been described with reference to preferred embodiments, a person skilled in the art will recognize that changes may be made in form and detail without departing from the spirit and scope of the invention.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A blood pump comprising:
   a casing having a top section, an inlet port and an outlet port, the inlet port being disposed substantially adjacent to and eccentric from the top section of the casing,
   at least one pivot bearing fixed in the casing,
   at least one impeller disposed in the casing, the at least one impeller comprising a rotatable shaft having an end,
   a pivot integrated with the end of the rotatable shaft and supported in the at least one pivot bearing for permitting rotation of the at least one impeller relative to the casing,
   vanes for forcing a fluid through the casing from the inlet port to the outlet port when the rotatable shaft rotates,
   a magnet, and
   magnetic drive means disposed outside the casing for cooperating with the magnet to rotate the at least one impeller,
   wherein at least one of the pivot and the pivot bearing comprises a ceramic material.

2. The blood pump of claim 1, wherein the pivot bearing comprises a first pivot bearing and further comprising a second pivot bearing fixed in the casing, wherein the rotatable shaft of the at least one impeller has two ends, each of the two ends having an integrated pivot and supported by one of the first and second pivot bearings and wherein at least one of the plurality of pivots and at least one of the first and second pivot bearings comprise a ceramic material.

3. The blood pump of claim 1, wherein the pivot defines a first radius of curvature and the pivot bearing defines a second radius of curvature and the ratio of the first radius of curvature to the second radius of curvature is approximately 1 to 4.

4. The blood pump of claim 1, wherein the vanes comprise a rotary vane section having a surface which faces the pivot and the pivot bearing, and further comprising vanes on the surface.

5. The blood pump of claim 1, wherein at least one of the pivots or the pivot bearings has a surface coated with diamond.

6. A blood pump comprising:
   a casing having an inlet port and an outlet port,
   at least one pivot bearing fixed in the casing,
   at least one impeller disposed in the casing, the at least one impeller comprising a rotatable shaft having an end, a pivot integrated with the end of the rotatable shaft and supported in the at least one pivot bearing for permitting rotation of the at least one impeller relative to the casing, vanes for forcing a fluid through the casing from the inlet port to the outlet port when the rotatable shaft rotates, a magnet, and magnetic drive means disposed outside the casing for cooperating with the magnet to rotate the at least one impeller, wherein at least one of the pivot and the pivot bearing comprises a ceramic material, and wherein the ceramic comprises zirconia as a principal constituent.

7. A blood pump comprising:

a casing having an inlet port and an outlet port, at least one pivot bearing fixed in the casing, at least one impeller disposed in the casing, the at least one impeller comprising a rotatable shaft having an end, a pivot integrated with the end of the rotatable shaft and supported in the at least one pivot bearing for permitting rotation of the at least one impeller relative to the casing, vanes for forcing a fluid through the casing from the inlet port to the outlet port when the rotatable shaft rotates, a magnet, and magnetic drive means disposed outside the casing for cooperating with the magnet to rotate the at least one impeller, wherein at least one of the pivot and the pivot bearing comprises a ceramic material, and wherein the ceramic comprises silicon nitride as a principal constituent.

8. A blood pump comprising:

a casing having an inlet port and an outlet port, at least one pivot bearing fixed in the casing, at least one impeller disposed in the casing, the at least one impeller comprising a rotatable shaft having an end, a pivot integrated with the end of the rotatable shaft and supported in the at least one pivot bearing for permitting rotation of the at least one impeller relative to the casing, vanes for forcing a fluid through the casing from the inlet port to the outlet port when the rotatable shaft rotates, a magnet, and magnetic drive means disposed outside the casing for cooperating with the magnet to rotate the at least one impeller, wherein at least one of the pivot and the pivot bearing comprises a ceramic material, wherein the ceramic comprises alumina as a principal constituent.

9. A blood pump comprising:

a casing having an inlet port and an outlet port, at least one pivot bearing fixed in the casing, at least one impeller disposed in the casing, the at least one impeller comprising a rotatable shaft having an end, a pivot integrated with the end of the rotatable shaft and supported in the at least one pivot bearing for permitting rotation of the at least one impeller relative to the casing, vanes for forcing a fluid through the casing from the inlet port to the outlet port when the rotatable shaft rotates, a magnet, and magnetic drive means disposed outside the casing for cooperating with the magnet to rotate the at least one impeller, wherein at least one of the pivot and the pivot bearing comprises a ceramic material, wherein the ceramic comprises silicon carbide as a principal constituent.

* * * * *